United States Patent
Nukatsuka et al.

(10) Patent No.: US 8,217,360 B2
(45) Date of Patent: Jul. 10, 2012

(54) NEUTRON MODERATOR, NEUTRON IRRADIATION METHOD, AND HAZARDOUS SUBSTANCE DETECTION APPARATUS

(75) Inventors: Shigehiro Nukatsuka, Tokyo (JP); Yasuhiro Iwamura, Kanagawa (JP); Michio Katoh, Tokyo (JP); Kazuya Nishimura, Tokyo (JP); Hidenori Sawamura, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 464 days.

(21) Appl. No.: 12/445,483

(22) PCT Filed: Sep. 21, 2007

(86) PCT No.: PCT/JP2007/068354
§ 371 (c)(1),
(2), (4) Date: Apr. 14, 2009

(87) PCT Pub. No.: WO2008/047529
PCT Pub. Date: Apr. 24, 2008

(65) Prior Publication Data
US 2010/0025594 A1   Feb. 4, 2010

(30) Foreign Application Priority Data
Oct. 16, 2006   (JP) .................................. 2006-281903

(51) Int. Cl.
*G01N 23/22* (2006.01)
(52) U.S. Cl. .................................................. 250/370.11
(58) Field of Classification Search ............... 250/269.3, 250/269.4, 269.5, 269.6, 269.7, 370.05, 370.09, 250/370.11, 390.01, 390.11, 393, 503.1, 250/518.1
See application file for complete search history.

(56) References Cited

U.S. PATENT DOCUMENTS

| | | | | |
|---|---|---|---|---|
| 3,089,958 | A * | 5/1963 | Janner | 376/254 |
| 3,126,481 | A * | 3/1964 | Whittier | 250/390.01 |
| 3,728,544 | A * | 4/1973 | Untermyer | 376/159 |
| 4,266,132 | A * | 5/1981 | Marshall, III | 250/359.1 |
| 4,599,515 | A * | 7/1986 | Whittemore | 250/390.1 |
| 4,682,043 | A * | 7/1987 | Marshall | 250/358.1 |
| 4,882,121 | A * | 11/1989 | Grenier | 376/159 |
| 5,098,640 | A * | 3/1992 | Gozani et al. | 376/166 |
| 5,388,128 | A | 2/1995 | Gozani | |

(Continued)

FOREIGN PATENT DOCUMENTS
JP   64-086047 A   3/1989
(Continued)

OTHER PUBLICATIONS

Korean Office Action dated Dec. 23, 2010, issued in correspoinding Korean Patent Application No. 10-2009-7007648.

(Continued)

*Primary Examiner* — David Porta
*Assistant Examiner* — Djura Malevic
(74) *Attorney, Agent, or Firm* — Westerman, Hattori, Daniels & Adrian, LLP

(57) ABSTRACT

A neutron moderator includes a neutron generator; a neutron moderating material arranged on one side of the neutron generator; a gamma ray shielding material covering an external surface of the neutron moderating material; and a thermal neutron absorbing material covering the external surface of the neutron moderating material except a side where the neutron generator is arranged.

4 Claims, 5 Drawing Sheets

U.S. PATENT DOCUMENTS

| | | | |
|---|---|---|---|
| 5,712,484 A * | 1/1998 | Harada et al. | 250/370.15 |
| 5,859,436 A * | 1/1999 | Harada et al. | 250/370.01 |
| 7,027,555 B2 * | 4/2006 | Proctor | 378/57 |
| 7,286,635 B2 * | 10/2007 | Proctor | 378/57 |
| 7,573,044 B2 * | 8/2009 | Norris | 250/390.04 |
| 2006/0126773 A1 * | 6/2006 | Haruyama | 376/159 |
| 2008/0017806 A1 * | 1/2008 | Norris | 250/390.04 |
| 2008/0156997 A1 * | 7/2008 | Kearfott | 250/390.04 |
| 2010/0061500 A1 * | 3/2010 | Lou et al. | 376/114 |

FOREIGN PATENT DOCUMENTS

| | | |
|---|---|---|
| JP | 01-189551 A | 7/1989 |
| JP | 08-234000 A | 9/1996 |
| JP | 08-292269 A | 11/1996 |

OTHER PUBLICATIONS

International Search Report of PCT/JP2007/068354, Mailing Date of Oct. 23, 2007.

Chinese Office Action dated May 12, 2011 issued in corresponding Chinese Patent Application No. 200780038606.2. English Translation.

Yang, Yi-Gang et al., "Study on the System of 14 MeV Neutron Generator-based Explosives Detection Using NaI(TI) and BGO Detectors," Journal of Isotopes, May 31, 2005, pp. 34-38, vol. 18, No. 1-2. English Abstract.

Cao, Xizheng et al., "Experimental Research on Detecting Explosives with Pulsed Fast/Thermal Neutron Analysis," Nuclear Techniques, Nov. 30, 2005, pp. 881-883, vol. 28, No. 11. English Abstract.

* cited by examiner

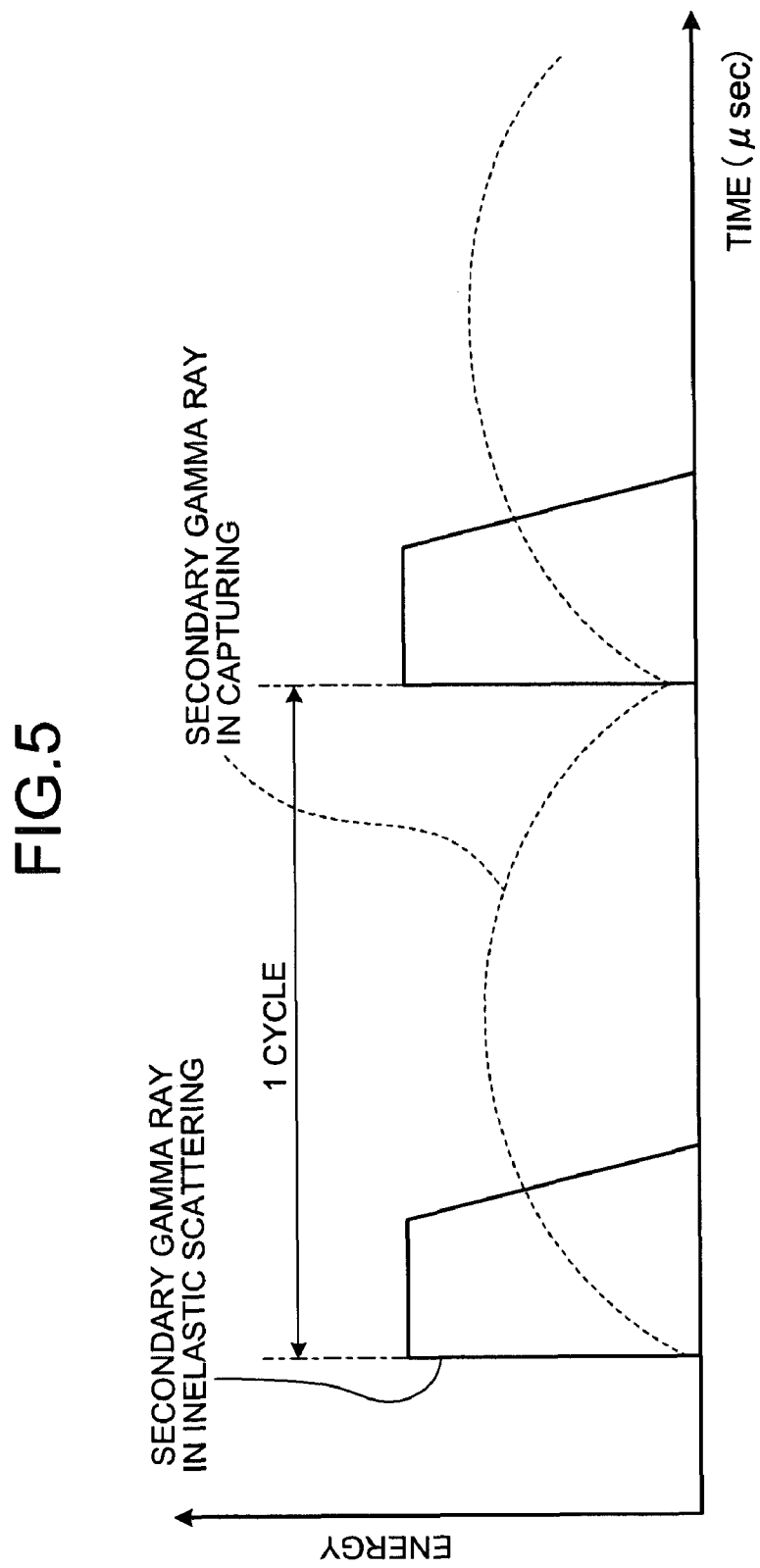

NEUTRON MODERATOR, NEUTRON IRRADIATION METHOD, AND HAZARDOUS SUBSTANCE DETECTION APPARATUS

TECHNICAL FIELD

The present invention relates to a neutron moderator that moderates extremely high-energy fast neutron generated by a neutron source to increase low energy neutron, and to a hazardous substance detection apparatus that is for inspecting hazardous substances such as explosives, utilizing such a neutron moderator.

BACKGROUND ART

In large public facilities such as stations, airports, harbors, baseball stadiums, soccer stadiums, event halls, and museums where a large number of people gather, security is ensured by checking luggage of users upon their admittance thereto to prevent hazardous substances, e.g., explosives, to be carried therein. Conventionally, neutron has been known to enable detection of explosives. Because many explosives include nitrogen as a constituent element, it has been suggested in developments of the past to detect an explosive based on presence and concentration of nitrogen. This is achieved by allowing fast neutron from a neutron generator to pass through a moderating material, thereby moderating the fast neutron down to thermal neutron, and irradiating the explosive with thermal neutrons and detecting energy of gamma ray produced thereby. However, recently, explosives having carbon, hydrogen, or oxygen as a constituent element but not nitrogen have been developed. Such explosives produce gamma ray upon being irradiated with fast neutron from a neutron generator, because of inelastic scattering of the fast neutron and each of the constituent elements thereof. Therefore, by detecting energy of such gamma ray, an explosive can be detected based on the concentration of each of these constituent elements.

An example of such a hazardous substance detection apparatus is disclosed in Patent Document 1 listed below. A composite cavity structure used for an explosive detection method according to the Patent Document 1 can moderate neutron from a high energy neutron source down to low energy thermal neutron. Because low energy thermal neutron reacts with nuclei used heavily in a luggage or a parcel having nitrogen housed therein to produce gamma ray, the gamma ray is detected and analyzed using a detector to detect the presence and concentration of the nitrogen, thus enabling detection of the explosive.

[Patent Document 1] Japanese Patent Application Laid-open No. S64-086047

DISCLOSURE OF INVENTION

Problem to be Solved by the Invention

However, a neutron moderating material also includes constituent elements such as carbon, hydrogen, oxygen, and nitrogen, that are same as those of an explosive. Therefore, if fast neutron emitted from a neutron generator is moderated down to thermal neutron by allowing the fast neutron to pass through a moderating material, and gamma ray produced when an explosive is irradiated with the thermal neutron is detected, the amount of the detected gamma ray would include the gamma ray produced from the neutron moderating material, mixed up with the gamma ray produced from the explosive. Therefore, the measurement would be less accurate, further reducing accuracy of detection of an explosive, thus causing a problem. Furthermore, if a constituent element of an explosive is detected based on gamma ray that is produced upon being irradiated with the thermal neutron, the amount of the detected gamma ray would include gamma ray produced from carbon, hydrogen, oxygen, and nitrogen existing in the air, in addition to the gamma ray produced from the explosive. Thus, the detection of an explosive would be less accurate.

The present invention is made to solve the problems described above. An object of the present invention is to provide a neutron moderator and a neutron irradiation method that enable necessary fast neutron and thermal neutron to be taken out, while suppressing secondary gamma ray produced in the neutron moderator so as to prevent detection thereof with an a detector, and preventing leakage of thermal neutron in directions other than an irradiation direction. Another object of the present invention is to provide a hazardous substance detection apparatus capable of detecting a hazardous substance with a high degree of accuracy by using the neutron moderator, regardless of the constituent elements of the hazardous substance.

Means for Solving Problem

A neutron moderator according to an aspect of the invention includes a neutron generator; a neutron moderating material arranged on one side of the neutron generator; a gamma ray shielding material covering an external surface of the neutron moderating material; and a thermal neutron absorbing material covering the external surface of the neutron moderating material except a side where the neutron generator is arranged.

In the neutron moderator, the gamma ray shielding material may include a first gamma ray shielding material covering the external surface of the neutron moderating material except the area where the neutron generator is arranged; and a second gamma ray shielding material arranged between the neutron generator and the neutron moderating material, and having a function to increase thermal neutron.

A neutron irradiation method according to another aspect of the invention includes emitting fast neutrons generated by a neutron generator forward; moderating fast neutron, which is generated by the neutron generator and emitted backward, down to intermediate neutron, epithermal neutron, and thermal neutron; taking out only neutron that is reflected forward to emit the reflected neutron forward along with the fast neutron; and shielding secondary gamma ray generated upon moderating of the fast neutron.

A hazardous substance detection apparatus according to another aspect of the invention includes an inspection chamber where an inspection target is insertable and removable; a thermal neutron absorbing material arranged so as to surround the inspection chamber; a neutron generator arranged facing the inspection target in the inspection chamber; a neutron moderating material arranged at an opposing side of the inspection target with respect to the neutron generator; a gamma ray shielding material covering an external surface of the neutron moderating material; and a gamma ray detector that detects gamma ray generated from the inspection target.

In the hazardous substance detection apparatus the gamma ray shielding material may includes a first gamma ray shielding material covering the external surface of the neutron moderating material except the area facing the neutron generator; and a second gamma ray shielding material arranged between the neutron generator and the neutron moderating material, and having a function to increase thermal neutron.

In the hazardous substance detection apparatus, the gamma ray detector may include a germanium semiconductor detector and a bismuth germanate oxide scintillator detector.

The hazardous substance detection apparatus may further include a pair of neutron detectors arranged facing each other at both sides of the inspection target.

EFFECT OF THE INVENTION

A neutron moderator according to an aspect of the invention includes a neutron moderating material arranged on one side of a neutron generator; a gamma ray shielding material covering an external surface of the neutron moderating material; and a thermal neutron absorbing material covering the external surface of the neutron moderating material except a side where the neutron generator is arranged. Fast neutron is emitted from the neutron generator forward as well as backward and laterally. The fast neutron that is emitted backward and laterally is moderated down to intermediate neutron, epithermal neutron, and thermal neutron by way of the neutron moderating material, and a portion of these neutrons are reflected forward. The remaining thermal neutron is absorbed by the thermal neutron absorbing material. The gamma ray shielding material prevents external leakage of secondary gamma ray that is generated when the fast neutron is moderated. Accordingly, generated secondary gamma ray can be suppressed, and necessary fast and thermal neutrons can reliably be taken out and applied for irradiation.

A neutron moderator according to another aspect of the invention includes, as gamma ray shielding materials, a first gamma ray shielding material covering the external surface of the neutron moderating material except the area where the neutron generator is arranged; and a second gamma ray shielding material arranged between the neutron generator and the neutron moderating material and having a function to increase thermal neutron. Fast neutrons is moderated down to intermediate neutron, epithermal neutron, and thermal neutron by way of the neutron moderating material. The secondary gamma ray generated at this time is suppressed by the first and the second gamma ray shielding materials. A portion of the intermediate neutron and the epithermal neutron out of the moderated neutrons is further moderated by the second gamma ray shielding material. The thermal neutron is increased in number and emitted forward. Accordingly, thermal neutron can be efficiently taken out and applied for irradiation.

A neutron irradiation method according to another aspect of the invention includes emitting fast neutron generated by a neutron generator forward; moderating fast neutron, which is generated by the neutron generator and emitted backward, down to intermediate neutron, epithermal neutron, and thermal neutron; taking out only neutron that is reflected forward to be emitted forward along with the fast neutron; and shielding secondary gamma ray generated upon moderating of the fast neutron. Therefore, it is possible to reliably take out the fast neutron generated by the neutron generator and the reflected neutron moderated by way of the neutron moderating material, and to emit these neutrons forward.

A hazardous substance detection apparatus according to another aspect of the invention includes an inspection chamber where an inspection target is insertable and removable; a thermal neutron absorbing material arranged so as to surround the inspection chamber; a neutron generator arranged facing the inspection target in the inspection chamber; a neutron moderating material arranged at an opposing side of the inspection target with respect to the neutron generator; a gamma ray shielding material covering an external surface of the neutron moderating material; and a gamma ray detector that detects gamma ray generated from the inspection target. The fast neutrons emitted from the neutron generator are emitted to the inspection target, as well as backward and laterally. The fast neutron that is emitted backward and laterally is moderated down to intermediate neutron, epithermal neutron, and thermal neutron by way of the neutron moderating material. A portion of the neutrons is reflected and the inspection target is irradiated therewith, while remaining thermal neutron is absorbed by the thermal neutron absorbing material. The gamma ray shielding material prevents external radiation of secondary gamma ray that is generated when the fast neutron is moderated. As a result, it is possible to irradiate the inspection target with the fast neutron and the thermal neutron. Furthermore, by detecting the gamma ray generated upon irradiation by the gamma ray detector, it is also possible to detect a hazardous substance based on energy strength of the gamma ray. Therefore, the hazardous substance can be detected with a high degree of accuracy, regardless of a constituent element thereof, thus enabling improvement of detection accuracy.

A hazardous substance detection apparatus according to another aspect of the invention includes, as the ray shielding material, a first gamma ray shielding material covering the external surface of the neutron moderating material except for an area facing the neutron generator; and a second gamma ray shielding material arranged between the neutron generator and the neutron moderating material, and having a function to increase thermal neutron. With this configuration, the fast neutron can be moderated down to intermediate neutron, epithermal neutron, and thermal neutron, and secondary gamma ray generated at this time is suppressed by way of the first and the second gamma ray shielding materials. Therefore, the secondary gamma ray does not get mixed up with that generated when the inspection target is irradiated with the fast neutron and the thermal neutron. At the same time, the thermal neutron is increased by the second gamma ray shielding material and reflected forward. Accordingly, detection accuracy of a hazardous substance can be improved.

A hazardous substance detection apparatus according to another aspect of the invention includes a germanium semiconductor detector and a bismuth germanate oxide scintillator detector as the gamma ray detectors. The germanium semiconductor detector ensures a high resolution of the detected gamma ray. At the same time, the bismuth germanate oxide scintillator detector, which is inferior to the germanium semiconductor detector in resolution but has high sensitivity, ensures highly accurate signal strength of the detected gamma ray. Accordingly, detection accuracy of the gamma ray can be improved.

A hazardous substance detection apparatus according to another aspect of the invention of includes a pair of neutron detectors arranged facing each other at both sides of the inspection target. Accordingly, by allowing the pair of the neutron detectors to detect the neutrons generated from the inspection target almost simultaneously, it is possible to reliably detect the presence of a nuclear material in the inspection target.

BRIEF DESCRIPTION OF DRAWINGS

FIG. 5 is a schematic timing chart of detection of secondary gamma ray in the hazardous substance detection apparatus according to the embodiment.

EXPLANATIONS OF LETTERS OR NUMERALS 11 neutron generator
12 neutron moderating material
13 first gamma ray shielding material (gamma ray shielding material)
14 second gamma ray shielding material (gamma ray shielding material)
15 thermal neutron absorbing material
21 inspection chamber
23 third gamma ray shielding material (gamma ray shielding material)
24 germanium semiconductor detector, Ge detector (gamma ray detector)
25 bismuth germanate oxide scintillator detector, BGO detector (gamma ray detector)
26 neutron detectors
A inspection target

BEST MODE(S) FOR CARRYING OUT THE INVENTION

The preferred embodiments of a neutron moderator, a neutron irradiation method, and a hazardous substance detection apparatus according to the present invention will now be described in detail with reference to the accompanying drawings. It should be understood that these embodiments are not intended to limit the scope of the present invention.

Embodiment

Figure 1:
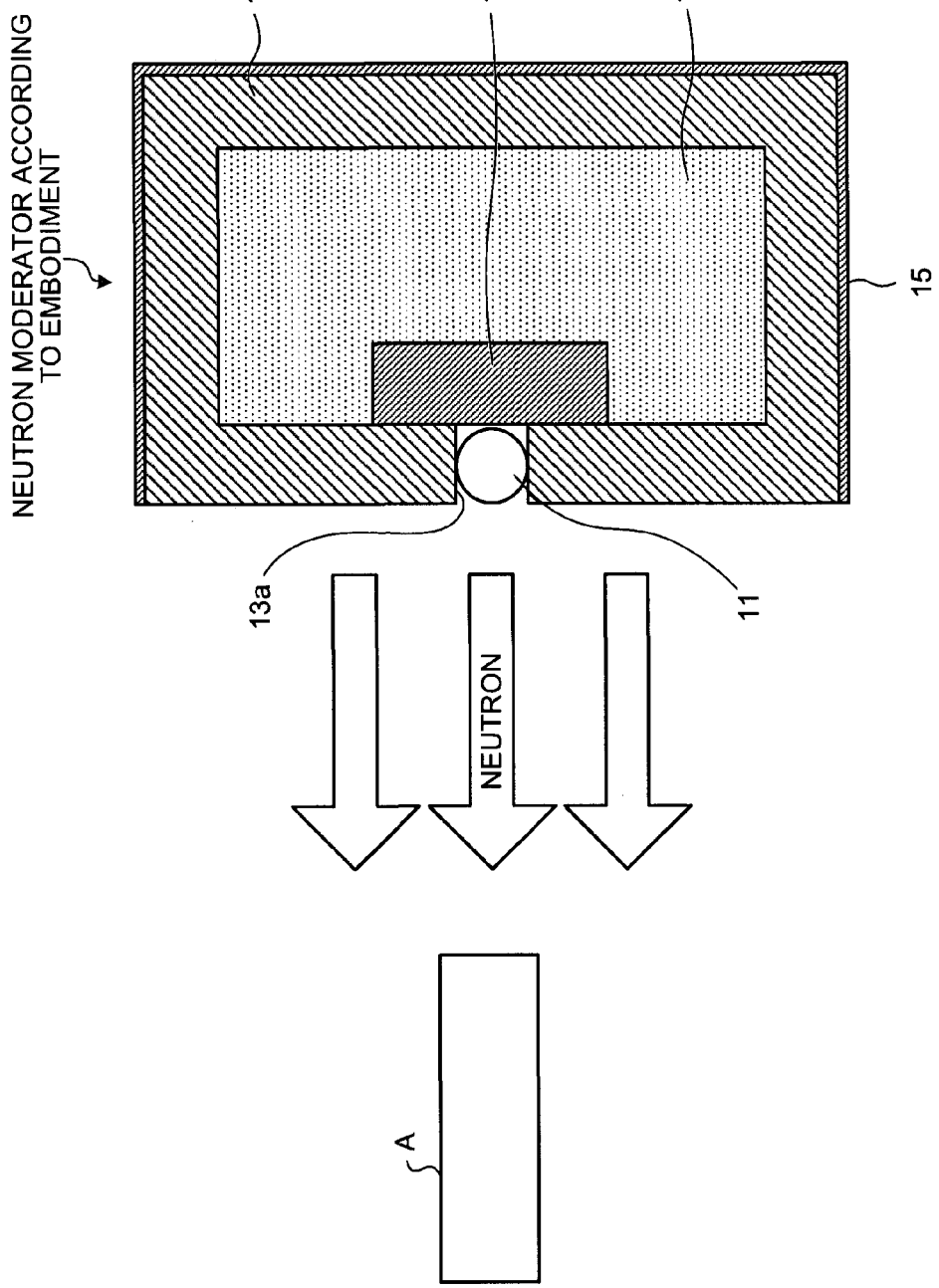
FIG. 1 is a schematic side view of a neutron moderator according to an embodiment of the present invention.
Figure 2:
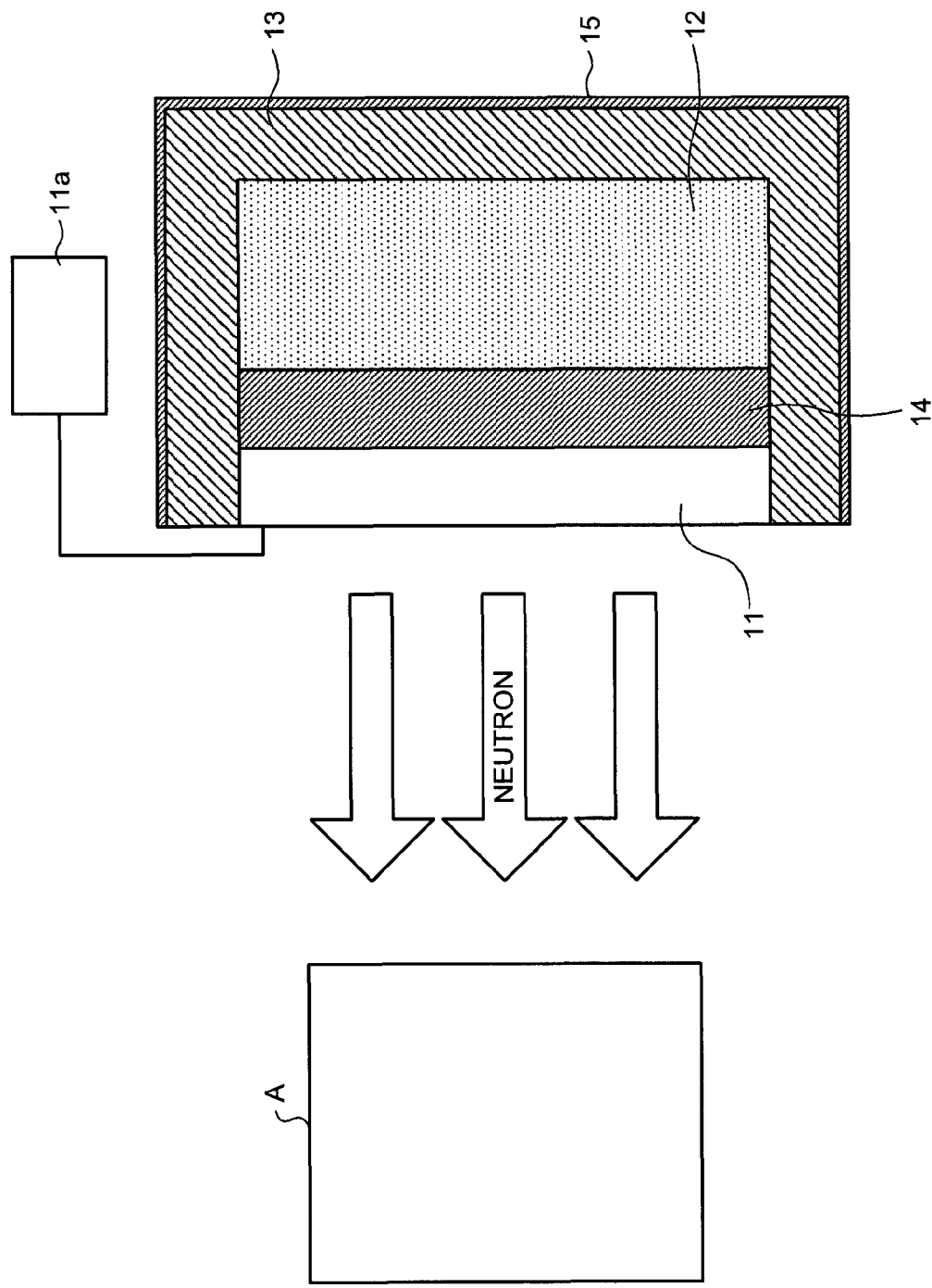
FIG. 2 is a schematic plan view of the neutron moderator according to the embodiment.
Figure 3:
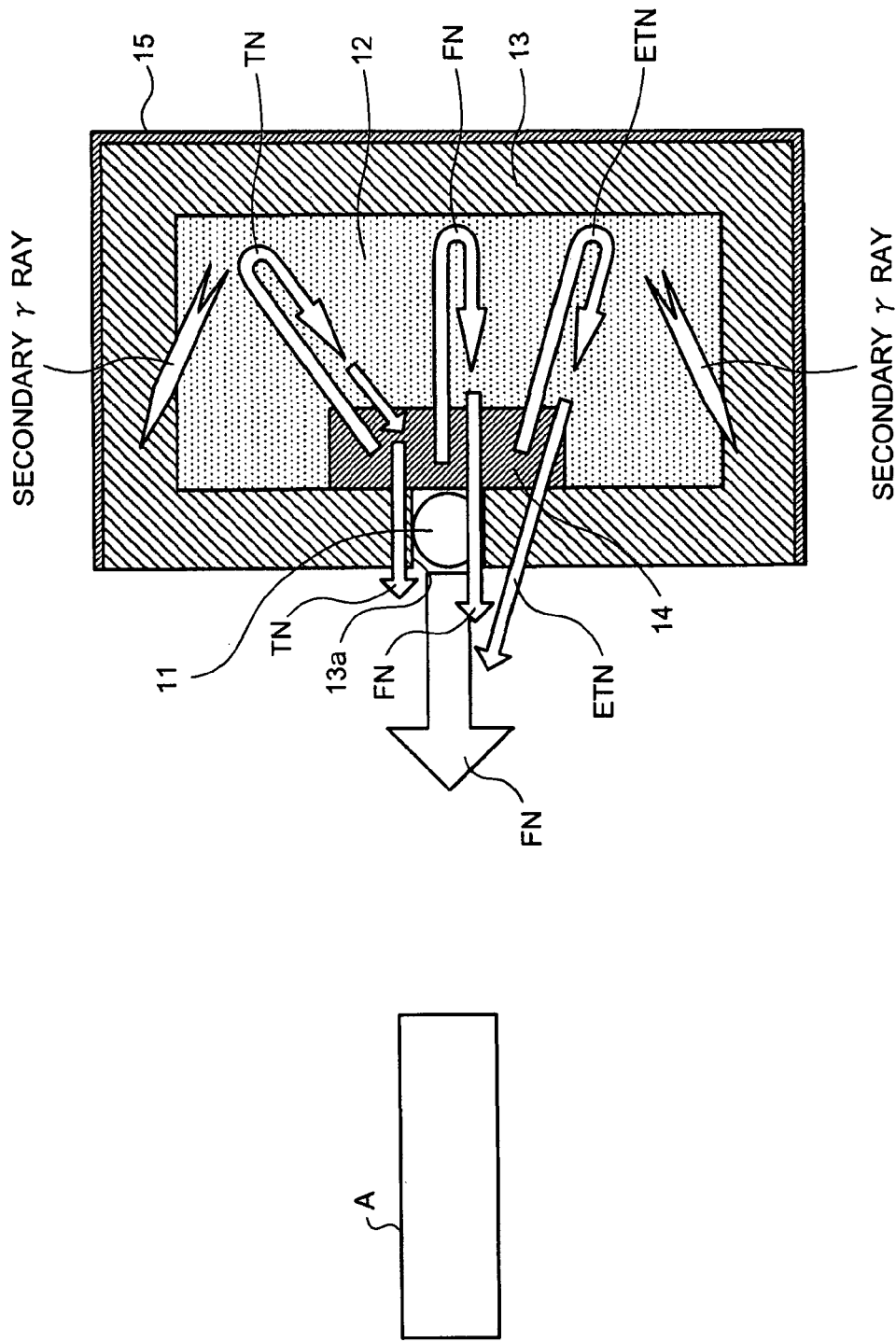
FIG. 3 is a schematic drawing of a fast neutron and thermal neutron irradiation method using the neutron moderator according to the embodiment.
Figure 4:
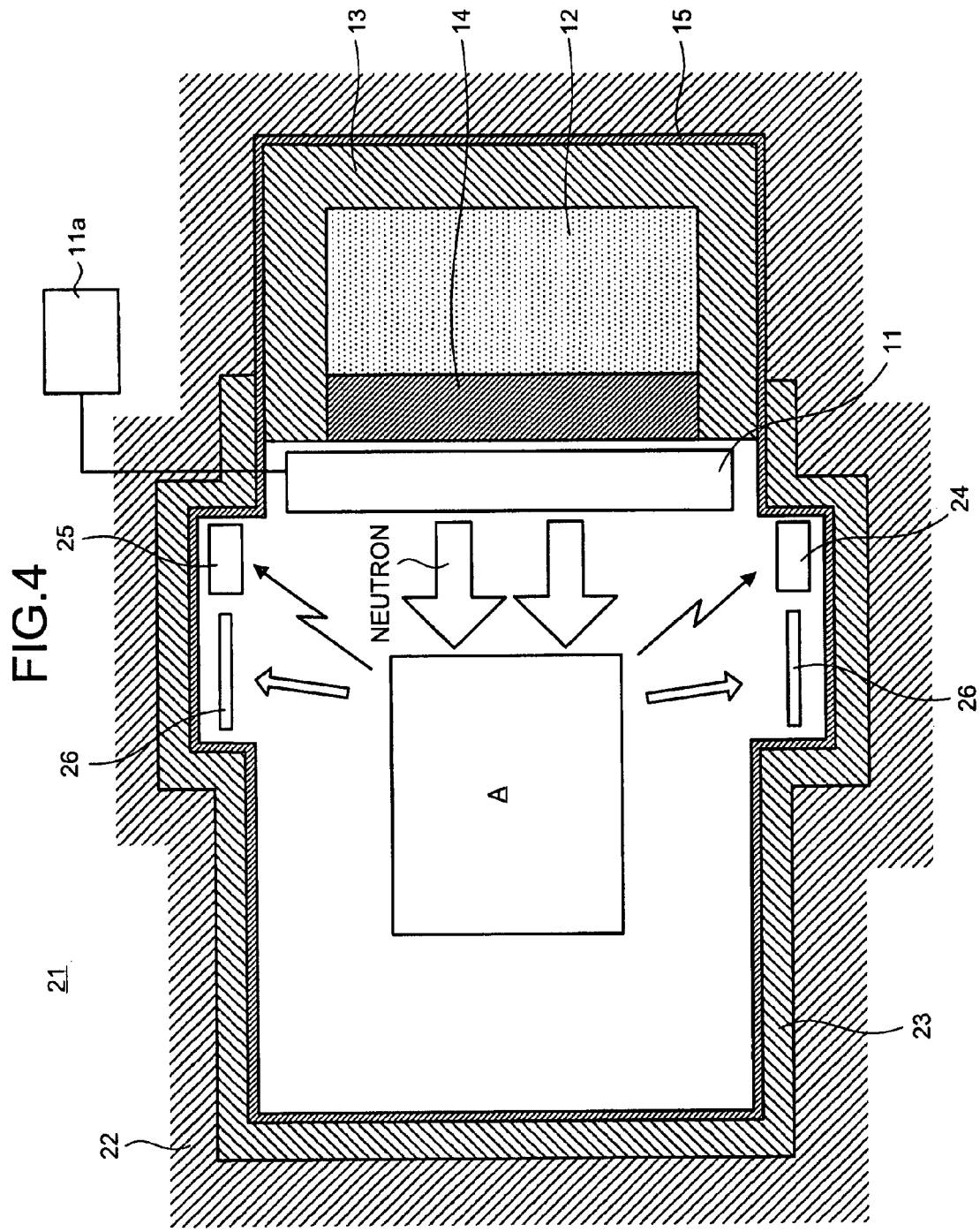
FIG. 4 is a schematic drawing of a hazardous substance detection apparatus utilizing the neutron moderator according to the embodiment.

FIG. 1 is a schematic side view of a neutron moderator according to an embodiment of the present invention; FIG. 2 is a schematic plan view of the neutron moderator according to the embodiment; FIG. 3 is a schematic drawing of a fast and thermal neutron irradiation method using the neutron moderator according to the embodiment; FIG. 4 is a schematic drawing of a hazardous substance detection apparatus utilizing the neutron moderator according to the embodiment; and FIG. 5 is a schematic timing chart of detection of secondary gamma ray in the hazardous substance detection apparatus according to the embodiment.

First, the neutron moderator according to the present invention will be explained. As shown in FIGS. 1 and 2, a neutron generator 11 is a material or an apparatus that produces neutron, and types thereof include those based on spontaneous fission, D-T reactions, D-D reactions, or ($\alpha$, n) reactions. The neutron generator 11 is tubular in shape, and connected to a power unit 11a, enabling emission of fast neutron in all surrounding directions. A neutron moderating material 12 is arranged on one side of the neutron generator 11 (on the right side in FIGS. 1 and 2). This neutron moderating material 12 is made of polyethylene, for example, and moderates the fast neutron emitted from the neutron generator 11 to convert the fast neutron into fast neutron, intermediate neutron, slow neutron, epithermal neutron, and thermal neutron. For the neutron moderating material 12, materials other than polyethylene as mentioned above may also be used, such as a material containing polyethylene (e.g., boron loaded polyethylene), a material containing graphite or carbon (e.g., boron carbide), or a fluorine compound (e.g., lithium fluoride, magnesium fluoride, or gadolinium fluoride).

A first gamma ray shielding material 13 and a second gamma ray shielding material 14 are arranged so as to surround this neutron moderating material 12 as gamma ray shielding materials covering the neutron moderating material 12. The first gamma ray shielding material 13 is arranged so as to cover the external surface of the neutron moderating material 12 except the area where the neutron generator 11 is arranged. The first gamma ray shielding material 13 attenuates, absorbs, and shields secondary gamma ray produced when the fast neutron emitted from the neutron generator 11 is moderated by way of the neutron moderating material 12, thus preventing external leakage thereof. This first gamma ray shielding material 13 is made of a heavy metal containing a material such as lead, zirconium, tungsten, molybdenum, or iron. The second gamma ray shielding material 14, on the contrary, is arranged between the neutron generator 11 and the neutron moderating material 12. The entire surface of the neutron moderating material 12 is covered with the first gamma ray shielding material 13 and the second gamma ray shielding material 14. The second gamma ray shielding material 14 is arranged so as to close a thermal neutron emitting opening 13a that is formed in the first gamma ray shielding material 13 correspondingly to the neutron moderating material 12. The second gamma ray shielding material 14 has a function to moderate intermediate neutron and epithermal neutron, and a function to increase thermal neutron with which an irradiated material is irradiated. It is most preferable to use bismuth for the second gamma ray shielding material 14. Alternatively, the second gamma ray shielding material 14 may be formed of a heavy metal containing a material such as lead, zirconium, tungsten, molybdenum, or iron.

In addition, a thermal neutron absorbing material 15 is arranged so as to surround the neutron moderating material 12, the first gamma ray shielding material 13, and the second gamma ray shielding material 14 so that these shielding materials are covered therewith, except the side where the neutron generator 11 is arranged. The thermal neutron absorbing material 15 absorbs a portion of the thermal neutron, which is the fast neutron emitted from the neutron generator 11 and moderated by the neutron moderating material 12, thereby preventing external leakage thereof from the lateral and the rear sides of the neutron generator 11. In this arrangement, it is also possible to cover the external surface of the neutron moderating material 12 with the thermal neutron absorbing material 15, and to further cover the external surface of the thermal neutron absorbing material 15 with the first gamma ray shielding material 13.

In the neutron moderator according to the embodiment, an inspection target A is irradiated with at least the fast neutron and the thermal neutron.

That is, as shown in FIG. 3, fast neutron FN generated at the neutron generator 11 is emitted forward, as well as backward and laterally. The fast neutron FN that is emitted backward and laterally is moderated down to epithermal neutron (ETN) (including intermediate neutron) and thermal neutron (TN) while the fast neutron FN passes through the neutron moderating material 12. The epithermal neutron ETN, the thermal neutron TN and the fast neutron FN are reflected forward; a portion of the fast neutron FN and the epithermal neutron ETN pass through the first gamma ray shielding material 13 and the thermal neutron absorbing material 15; and a portion of the thermal neutrons TN is absorbed by the thermal neutron absorbing material 15. At this time, the reflected fast neutron FN and the epithermal neutron (these includes intermediate neutron) ETN are further moderated while these neutrons pass through the second gamma ray shielding material 14, and these neutrons are moderated down to thermal neutron TN. The thermal neutron TN is increased. Secondary gamma ray (γ ray) that is produced while the fast neutron FN is moderated by way of the neutron moderating material 12, is shielded by the first gamma ray shielding material 13 and the second gamma ray shielding material 14.

Therefore, the inspection target A can be irradiated with the fast neutron FN that is directly emitted from the neutron generator 11, as well as with the reflected fast neutron FN, the reflected epithermal neutron ETN, and the reflected thermal neutron TN.

A hazardous substance detection apparatus utilizing the above-described neutron moderator according to the embodiment will be now explained. As shown in FIG. 4, an inspection chamber 21 is formed with surrounding concrete walls 22 with a predetermined thickness, and includes an insertion-and-removal opening, not shown, that enables insertion and removal of the inspection target A. In this case, the concrete walls 22 are preferably made of concrete including boron or lead, for example; however, the concrete walls may include polyethylene, a material including polyethylene (e.g., boron loaded polyethylene), a material including graphite or carbon (e.g., boron carbide), or a fluorine compound (e.g., lithium fluoride, magnesium fluoride, or gadolinium fluoride). The thermal neutron absorbing material 15, which is described above, is arranged on the entire surface of internal walls of the inspection chamber 21.

The neutron generator 11 is arranged on one side of the inspection chamber 21, facing the inspection target A; and the neutron moderating material 12 is arranged at an opposing side of the inspection target A with respect to the neutron generator 11. The first gamma ray shielding material 13 is arranged so as to cover the external surface of the neutron moderating material 12 in cohesion with the thermal neutron absorbing material 15, except for an area facing the neutron generator 11; and the second gamma ray shielding material 14 that has the function to increase thermal neutron is arranged between the neutron generator 11 and the neutron moderating material 12. A third gamma ray shielding material 23 that is made of a material same as the first gamma ray shielding material 13 is arranged between the concrete walls 22 of the inspection chamber 21 and the thermal neutron absorbing material 15, except the area where the first gamma ray shielding material 13 is arranged. The third gamma ray shielding material 23 may be arranged on the internal surface of the thermal neutron absorbing material 15.

A germanium semiconductor detector (hereinafter, "Ge detector") 24 and a bismuth germanate oxide scintillator detector (hereinafter, "BGO detector") 25 are arranged as gamma ray detectors for detecting the gamma ray (γ ray) emitted from the inspection target A in the inspection chamber 21. In this case, the Ge detector 24 and the BGO detector 25 are arranged facing each other at each side of the area where the inspection target A faces the neutron generator 11, and are covered with cadmium. The Ge detector 24 measures an energy spectrum of gamma ray, and has highly accurate resolution for the detected gamma ray. Similarly, the BGO detector 25 measures an energy spectrum of gamma ray, and has highly accurate sensitivity to the detected gamma ray.

In addition, a pair of neutron detectors 26 is arranged to detect neutron emitted from the inspection target A in the inspection chamber 21. This pair of the neutron detectors 26 is arranged facing each other at each side of the inspection target A in adjacent to the Ge detector 24 and the BGO detector 25, respectively, at an equal distance thereto. The neutron detectors 26 are able to measure the number of neutrons emitted from the inspection target A simultaneously.

In the hazardous substance detection apparatus according to the embodiment having the structure described above, when the neutron generator 11 is operated with the inspection target A at the predetermined position in the inspection chamber 21, that is, facing the neutron generator 11 as shown in FIGS. 3 and 4, the fast neutron FN is emitted forward, toward the inspection target A. At the same time, the fast neutron FN is also emitted laterally and backward, toward the neutron moderating material 12. The fast neutron FN emitted laterally and backward is moderated by the neutron moderating material 12 while passing therethrough, and the fast neutron is turned into epithermal neutron ETN and thermal neutron TN. The fast neutron FN, the epithermal neutron ETN, and the thermal neutron TN are reflected forward upon moderating the thereof; a portion of the fast neutron FN and the epithermal neutron ETN passes through the first gamma ray shielding material 13 and the thermal neutron absorbing material 15; and a portion of the thermal neutron TN is absorbed by the thermal neutron absorbing material 15. At this time, the reflected thermal neutron TN is increased by the second gamma ray shielding material 14 while passing therethrough. Secondary gamma ray (γ ray) that is produced while the fast neutrons FN is moderated by the neutron moderating material 12, is shielded by the first gamma ray shielding material 13 and the secondary gamma ray shielding material 14.

Therefore, the inspection target A is irradiated with the fast neutron FN that is directly emitted from the neutron generator 11, as well as with the fast neutron FN, the epithermal neutron ETN, and the thermal neutron TN that are moderated by the neutron moderating material 12 and reflected. When the inspection target A is irradiated with the fast neutron FN and the epithermal neutron ETN, the energy of neutrons are given to the nuclei, while the neutrons and the nuclei interact. The excited nuclei generate secondary gamma ray. The secondary gamma ray is generated by processes that can be generally classified into two.

One of the processes is an inelastic scattering reaction of the fast neutron FN and the epithermal neutron ETN with nuclei. In this process, a part of the energy of the neutron is given to the nuclei, mainly generating secondary γ ray having energy lower than the energy given. The inelastic scattering reaction of the gamma ray is mainly caused by neutrons having energy higher than thermal neutron. Because the reaction occurs repeatedly until the energy of the neutron decreases below the energy level of the thermal neutron, a large amount of gamma ray is produced, although the energy of the generated gamma ray is low.

Another process is a capture reaction of the thermal neutron TN, or the thermal neutron that is the fast neutron FN and the epithermal neutron ETN whose energy levels are reduced as a result of the inelastic scattering. In this process, neutron is once captured by nuclei, and the secondary gamma ray (called capture gamma ray) is released after a nuclear transformation has occurred. Therefore, the released gamma ray is released with much higher energy than the energy that has been given. In other words, in the inelastic scattering reaction, scattering occurs because the velocity of the neutron is too fast to be captured by nuclei. After repeating scattering, the neutron is moderated enough so that the neutron can be captured by the nuclei more easily.

The Ge detector 24 and the BGO detector 25 detect the energy spectrum of the secondary gamma ray, which is generated when the inspection target A is irradiated with the fast neutron FN, the epithermal neutron ETN, and the thermal neutron, in every cycle successively. As a result, as shown in FIG. 5, the inelastic scattering gamma ray generated from the inelastic scattering reaction of the fast neutron FN and the epithermal neutron ETN with the nuclei are generated in a large volume at an early stage of a cycle. The capture gamma ray generated from the elastic scattering reaction (capture reaction) of the thermal neutron TN with the nuclei is generated relatively slowly in a middle stage of a cycle.

Accordingly, the Ge detector 24 and the BGO detector 25 detect the energy spectrum of the secondary gamma ray (inelastic gamma ray) produced when the inspection target A is irradiated with the fast neutron FN and the epithermal neutron ETN, as well as the energy spectrum of the secondary gamma ray (capture gamma ray) produced when the inspection target A is irradiated with the thermal neutron TN. Thereby, an explosive can be detected by way of the energy of the secondary gamma ray based on the type of constituent elements (carbon, hydrogen, oxygen, or nitrogen) and concentration of the inspection target A.

If the inspection target A is made of a nuclear material (e.g., uranium or plutonium), the material is going through spontaneous fissions even without being irradiated with neutron. In a spontaneous fission reaction, two or more neutron particles can be generated simultaneously in different directions. By measuring the number of neutron particles generated from the inspection target A using the pair of the neutron detectors 26 simultaneously, it can be determined whether the inspection target A is made of a nuclear material that is going through spontaneous fissions.

The thermal neutron TN moderated by the neutron moderating material 12 are reflected toward the inspection target A; and other thermal neutron TN is absorbed by the thermal neutron absorbing material 15 and disappear. Therefore, the thermal neutron TN is prevented from being emitted in a direction other than toward the inspection target A, and from causing a reaction with the air. Thus, generation of detection noises at the Ge detector 24 and the BGO detector 25 is suppressed. On the contrary, the fast neutron FN and the epithermal neutron ETN pass through the thermal neutron absorbing material 15; however, even if these neutrons react with the air, there are very few reactions that result in detection noises at the Ge detector 24 and the BGO detector 25. The secondary gamma ray, generated when the fast neutron FN is moderated by the neutron moderating material 12, is blocked by the first gamma ray shielding material 13; therefore, external leakage thereof is prevented. Accordingly, misdetection by the Ge detector 24 and the BGO detector 25 is prevented.

As described above, in the neutron moderator and the neutron irradiation method according to the embodiment, the neutron moderating material 12 is arranged on one side of the neutron generator 11; the gamma ray shielding materials 13 and 14 are arranged so as to cover the external surface of the neutron moderating material 12; and the thermal neutron absorbing material 15 is arranged so as to cover the external surface of the neutron moderating material 12 except for the side where the neutron generator 11 is arranged.

Therefore, the fast neutron emitted from the neutron generator 11 is emitted forward as well as backward and laterally; the fast neutron emitted backward and laterally is moderated by the neutron moderating material 12; a portion of the thermal neutron is reflected forward; the remaining thermal neutron is absorbed by the thermal neutron absorbing material 15; the gamma ray shielding materials 13 and 14 prevent external leakage of the secondary gamma ray generated while the fast neutron is being moderated. Accordingly, the amount of generated secondary gamma ray can be reduced, and the necessary fast neutron and thermal neutron can be reliably taken out for irradiation.

Furthermore, in the neutron moderator according to the embodiment, the first gamma ray shielding material 13 is provided so as to cover the external surface of the neutron moderating material except the area where the neutron generator 11 is arranged; and the second gamma ray shielding material 14, having the function to increase thermal neutrons, is arranged between the neutron generator 11 and the neutron moderating material 12. Therefore, the fast neutrons is moderated down to thermal neutron by way of the neutron moderating material 12, and the secondary gamma ray generated at this time is suppressed by the first and the second gamma ray shielding materials 13 and 14. The moderated intermediate neutron, the epithermal neutron, and the thermal neutron with the number thereof increased by the second gamma ray shielding material 14, are emitted forward. Accordingly, the generated thermal neutron can be efficiently taken out and applied for irradiation.

Still furthermore, the hazardous substance detection apparatus according to the embodiment includes the inspection chamber 21 where the inspection target A can be inserted and removed; the thermal neutron absorbing material 15 arranged around the inspection chamber 21; the neutron generator 11 arranged facing the inspection target A in the inspection chamber 21; the neutron moderating material 12 arranged at the opposing side of the inspection target with respect to the neutron generator 11; the gamma ray shielding materials 13 and 14 covering the external surface of the neutron moderating material 12; and the Ge detector 24 and the BGO detector 25 that detect the gamma ray generated from the inspection target A.

Therefore, the fast neutron emitted from the neutron generator 11 is emitted toward the inspection target A as well as backward and laterally; the fast neutron emitted backward and laterally is moderated down to the intermediate neutron, the epithermal neutron, and the thermal neutron by the neutron moderating material 12; a portion of the neutron is reflected forward, and emitted toward the inspection target A; the remaining thermal neutron is absorbed by the thermal neutron absorbing material 15; and the secondary gamma ray generated when the fast neutron is moderated is prevented from emitting outside by way of the gamma ray shielding materials 13 and 14. As a result, the inspection target A can be irradiated with the fast neutron and the thermal neutron. In addition, by detecting the secondary gamma ray generated at the time of the irradiation by the Ge detector 24 and the BGO detector 25, a hazardous substance can be detected based on energy of the generated secondary gamma ray. Accordingly, a type of the hazardous substance can be detected accurately regardless of the constituent element thereof. Thus, the detection accuracy can be improved.

Still furthermore, the hazardous substance detection apparatus according to the embodiment includes the first gamma ray shielding material 13 covering the external surface of the neutron moderating material 12 excluding the area facing the neutron generator; the second gamma ray shielding material 14 arranged between the neutron generator 11 and the neutron moderating material 12, and having the function to increase the thermal neutron; and the third gamma ray shielding material 23 covering the external surface of the inspection chamber 21. With this configuration, the fast neutron is moderated down to the thermal neutron by way of the neutron moderating material 12; and the secondary gamma ray generated at this time is suppressed by each of the gamma ray shielding materials 13, 14, and 23. Therefore, the secondary gamma ray does not get mixed up with the secondary gamma ray generated when the inspection target A is irradiated with the fast neutron and the thermal neutron, and the thermal neutron is emitted forward after being increased by the second gamma ray shielding material 14. Therefore, the detection accuracy of a hazardous substance can be improved.

Still furthermore, the hazardous substance detection apparatus according to the embodiment includes the germanium semiconductor detector 24 and the bismuth germanate oxide scintillator detector 25. Therefore, a highly accurate resolution can be ensured for the gamma ray detected by the germanium semiconductor detector 24, as well as a highly accurate sensitivity for the gamma ray detected by the bismuth germanate oxide scintillator detector 25.

Accordingly, detection accuracy of the gamma ray can be improved.

Still furthermore, the hazardous substance detection apparatus according to the embodiment includes a pair of the neutron detectors 26 arranged facing each other at both sides of the inspection target A. The pair of the neutron detectors 26 enables almost simultaneous detection of the neutrons produced from the inspection target A. Therefore, the presence of a nuclear material in the inspection target A can be reliably detected.

INDUSTRIAL APPLICABILITY

The neutron moderator, the neutron irradiation method, and the hazardous substance detection apparatus according to the present invention enable necessary fast neutron and thermal neutron to be taken out while suppressing generated secondary gamma ray. By irradiating an inspection target with these fast neutron and thermal neutron, a type of a hazardous substance can be detected with a high degree of accuracy regardless of a constituent thereof. Therefore, the present invention can be applied to any neutron moderator and hazardous substance detection apparatus.

The invention claimed is:

1. A neutron moderator comprising:
a neutron generator;
a neutron moderating material arranged behind the neutron generator;
a gamma ray shielding material covering an external surface of the neutron moderating material; and
a thermal neutron absorbing material covering the external surface of the neutron moderating material except a side where the neutron generator is arranged, wherein
the gamma ray shielding material comprises:
a first gamma ray shielding material covering the external surface of the neutron moderating material except the area where the neutron generator is arranged; and
a second gamma ray shielding material arranged between the neutron generator and the neutron moderating material and just behind the neutron generator, and having a function to increase thermal neutron.

2. A hazardous substance detection apparatus comprising:
an inspection chamber where an inspection target is insertable and removable;
a thermal neutron absorbing material arranged so as to surround the inspection chamber;
a neutron generator arranged facing the inspection target in the inspection chamber;
a neutron moderating material arranged at an opposing side of the inspection target with respect to the neutron generator;
a gamma ray shielding material covering an external surface of the neutron moderating material; and
a gamma ray detector that detects gamma ray generated from the inspection target, wherein
the gamma ray shielding material comprises:
a first gamma ray shielding material covering the external surface of the neutron moderating material except the area facing the neutron generator; and
a second gamma ray shielding material arranged between the neutron generator and the neutron moderating material and just behind the neutron generator, and having a function to increase thermal neutron.

3. The hazardous substance detection apparatus according to claim 2, wherein the gamma ray detector comprises a germanium semiconductor detector and a bismuth germanate oxide scintillator detector.

4. The hazardous substance detection apparatus according to claim 2, further comprising a pair of neutron detectors arranged facing each other at both sides of the inspection target.

* * * * *